United States Patent [19]

Cummings

[11] 4,304,587
[45] Dec. 8, 1981

[54] FORMULATIONS FOR IMPROVED PESTICIDE-FERTILIZER COMPOSITIONS

[75] Inventor: Gary L. Cummings, Oakland, Calif.

[73] Assignee: Stauffer Chemical Company, Westport, Conn.

[21] Appl. No.: 91,228

[22] Filed: Nov. 5, 1979

[51] Int. Cl.$^3$ .......................................... A01N 25/00
[52] U.S. Cl. .................................. 71/4; 71/DIG. 1; 424/222; 424/225
[58] Field of Search .................. 71/86, 3, 4, DIG. 1; 424/222, 225

[56] References Cited

U.S. PATENT DOCUMENTS

| | | | |
|---|---|---|---|
| 2,988,474 | 6/1961 | Szabo et al. | 424/222 |
| 3,048,703 | 7/1962 | Schegk et al. | 260/929 |
| 3,112,244 | 11/1963 | Goyette | 424/221 |
| 3,157,486 | 11/1964 | Harrison et al. | 71/93 |
| 3,268,393 | 8/1966 | Wilson | 424/225 |

OTHER PUBLICATIONS

Scott et al., Chemical Engineering Progress, vol. 63, No. 10 (1967), pp. 258–266.

Martens et al., Agronomy Journal, vol. 70 (6), 1978, pp. 1089–1098.

*Primary Examiner*—Catherine L. Mills

*Attorney, Agent, or Firm*—M. Henry Heines

[57] ABSTRACT

A novel composition is disclosed, comprising
(a) an aqueous solution of an N-P or N-P-K fertilizer and
(b) an attapulgite clay. The composition provides improved emulsion stability when combined with an emulsifiable concentrate of an organophosphorus compound of the formula

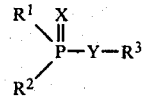

in which
$R^1$ is selected from the group consisting of $C_1$–$C_6$ alkyl, $C_1$–$C_6$ alkoxy, and $C_1$–$C_6$ alkylthio,
$R^2$ is selected from the group consisting of $C_1$–$C_6$ alkyl, $C_1$–$C_6$ alkoxy, and $C_1$–$C_6$ alkylthio,
$R^3$ is selected from the group consisting of $C_1$–$C_6$ alkyl, $C_2$–$C_8$ alkylthioalkyl, phenyl, and $C_7$–$C_{12}$ phenylthioalkyl, the phenyl rings optionally substituted with halogen, $C_1$–$C_3$ alkyl, nitro, or $C_1$–$C_3$ alkylsulfinyl,
X is oxygen or sulfur, and
Y is oxygen or sulfur.

13 Claims, No Drawings

FORMULATIONS FOR IMPROVED PESTICIDE-FERTILIZER COMPOSITIONS

BACKGROUND OF THE INVENTION

This invention relates to liquid fertilizers and organophosphorus pesticides. In particular, this invention relates to improved compositions for use in combining emulsifiable organophosphorus pesticide concentrates with aqueous fertilizer solutions for simultaneous field application.

An emulsifiable concentrate is a formulation of a chemical pesticide which is commonly used when the latter is intended for dilution at the field site. The formulation consists of a solution of the pesticide in a water-immiscible or partially water-miscible solvent which forms an emulsion upon dilution with water. Typical solvents include mineral oils, petroleum solvents, chlorinated hydrocarbons, alcohols, glycols, ethers, esters, and ketones. A surface active compound is frequently included in the concentrate to promote emulsification and emulsion stability.

An emulsifiable concentrate has an advantage over solid or semi-solid pesticide formulations in that it is a liquid and can thus be easily mixed with a liquid fertilizer so that the two can be applied to the field at the same time in a common piece of apparatus. Common fertilizer application equipment can be used to distribute a mixture containing both the fertilizer, preferably dissolved in water, and the emulsifiable pesticide concentrate, at prescribed dilution. Both fertilization and insect control are thereby achieved by a single application.

Among the liquid fertilizers in current use are those commonly known as "N-P" and "N-P-K" fertilizers. As their designations indicate, these fertilizers are identified by numbers corresponding to the relative quantities of nitrogen, phosphorus, and potassium salts, expressed as N, $P_2O_5$, and $K_2O$, respectively. Unfortunately, certain fertilizers when combined with the pesticide produce an emulsion of low stability. Sometimes, agitation inherent in the application equipment compensates for this. Tractors with spray booms, for example, which are used for broad area application, provide agitation through the pumps which feed the booms and the pump recycle lines which control the spray rate. Additional agitation is provided by paddles in the spray tanks of some tractors. Further agitation is achieved during the transfer of the fertilizer from the nurse tank in which it is brought to the field to the tractor spray tank in which it is combined with the pesticide mixture.

Each of these types of agitation helps to keep the dispersed phase from settling out of the pesticide-fertilizer emulsion. Unfortunately, these devices are not always sufficient to prevent the mixture from separating. When separation occurs, the result is an uneven application of the pesticide over the field. Equipment failure may also result as the feed lines become clogged with thick portions which have separated from the mixture. The problem is more pronounced, of course, when equipment containing no agitation mechanism is used.

The problem becomes particularly acute when fertilizer, pesticide, and crop seeds are placed in the soil simultaneously or in close succession. It is a common practice to use a simple piece of planting apparatus, such as a corn planter, to dig a furrow, deposit a row of seeds therein, and place a fluid mixture containing the pesticide and a high potency fertilizer in parallel bands on either side of the seeded row. This is commonly referred to as "split-boot" application. A fertilizer of relatively high salt content, commonly referred to as a "starter" fertilizer, is used to provide an extra impetus to initiate crop growth. The pesticide meanwhile serves to control insects which attack the seeds and seedlings. Unlike tractors equipped with pumps and boom sprayers for broad area application, many planters have no inherent agitation beyond that provided by the normal jostling which occurs as they proceed across the field. The fluid mixture is often fed to the soil by a squeeze pump which is driven by the tractor wheels, providing very little agitation. Separation of the pesticide suspension can occur readily in such an apparatus. In addition, the fertilizer itself tends to promote separation, because emulsion stability generally decreases with increasing fertilizer salt content.

SUMMARY OF THE INVENTION

It has now been discovered that the stability of an emulsion containing an organophosphorus pesticide and an N-P or N-P-K fertilizer is substantially enhanced by the inclusion of an attapulgite clay. The present invention thus resides in a fertilizer composition comprising
(a) an aqueous solution of an N-P or N-P-K fertilizer, and
(b) an attapulgite clay,
which produces an emulsion of improved stability when combined with an emulsifiable concentrate of an organophosphorus pesticide.

In another aspect, the invention resides in an emulsion composition comprising
(a) an aqueous solution of an N-P or N-P-K fertilizer,
(b) an attapulgite clay, and
(c) an organophosphorus compound of the formula

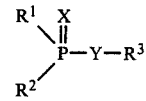

in which
R[1] is selected from the group consisting of $C_1$–$C_6$ alkyl, $C_1$–$C_6$ alkoxy, and $C_1$–$C_6$ alkylthio, preferably selected from the group consisting of $C_1$–$C_4$ alkoxy and $C_1$–$C_4$ alkylthio,
R[2] is selected from the group consisting of $C_1$–$C_6$ alkyl, $C_1$–$C_6$ alkoxy, and $C_1$–$C_6$ alkylthio, preferably selected from the group consisting of $C_1$–$C_4$ alkyl, $C_1$–$C_4$ alkoxy, and $C_1$–$C_4$ alkylthio,
R[3] is selected from the group consisting of $C_1$–$C_6$ alkyl, $C_2$–$C_8$ alkylthioalkyl, phenyl, and $C_7$–$C_{12}$ phenylthioalkyl, preferably selected from the group consisting of $C_1$–$C_3$ alkyl, $C_2$–$C_6$ alkylthioalkyl, phenyl, and $C_7$–$C_9$ phenylthioalkyl, the phenyl rings optionally substituted with halogen, $C_1$–$C_3$ alkyl, nitro, or $C_1$–$C_3$ alkylsulfinyl,
X is oxygen or sulfur, and
Y is oxygen or sulfur.

In still another aspect, the invention resides in a method for simultaneously enhancing crop growth and controlling insects residing in soil comprising applying to the soil an emulsion composition comprising
(a) a crop growth enhancing amount of an aqueous solution of an N-P or N-P-K fertilizer,
(b) an attapulgite clay, and
(c) an insecticidally effective amount of an organophosphorus compound of the above formula.

As used in this specification, the term "alkyl" denotes a saturated hydrocarbon radical of straight or branched chain containing the specified number of carbon atoms. The carbon atom ranges are intended to be inclusive of their upper and lower limits.

The term "halogen" is intended to include fluorine, chlorine, bromine, and iodine. Chlorine and bromine are preferred, and chlorine is particularly preferred.

The term "crop growth enhancing amount" denotes any quantity of fertilizer which causes an increase in the size of the crop plants or in their rate of growth as a result of such quantity being applied to the soil in any conventional manner. Such increases can result from fertilizer applications before the seeds are planted, while the seeds are being planted, or after planting has taken place.

The term "insecticidally effective amount" denotes any quantity of pesticide which when applied to soil in any conventional manner causes death or a substantial inhibition of the metabolic functions of a significant portion of the insect pest population residing therein.

The term "attapulgite clay" is used herein to include any of the class of clays or clay-containing materials based on the mineral attapulgite. This mineral, which is mined principally in southwest Georgia and northeast Florida, is a hydrated aluminum silicate in a lattice structure which also contains magnesium. Attapulgite crystals have an acicular configuration and occur as bundles of laths, the individual laths attaining a maximum length of about 4 to 5 microns, a maximum thickness of about 50 to 100 Angstroms, and a width ordinarily two to three times the thickness. An average chemical analysis of a typical attapulgite clay is as follows:

| | |
|---|---|
| $SiO_2$ | 60% (by weight) |
| $Al_2O_3$ | 10% |
| MgO | 10% |
| $Fe_2O_3$ | 4% |
| CaO | 2% |
| $K_2O$ | 1% |
| $TiO_2$ | 0.5% |
| other | balance |

Attapulgite clays are available in dry form as well as in beneficiated form, in which they are predispersed in water with optional additional stabilizing components. Attapulgite granules which break down into small particles when contacted with water can also be used.

DESCRIPTION OF THE PREFERRED EMBODIMENTS

According to the present invention, an attapulgite clay is combined with an aqueous solution of an N-P or N-P-K fertilizer and an emulsifiable organophosphorus pesticide concentrate to provide an emulsion of improved stability for a single field application. To achieve the fastest dispersion of the clay in the fluid mixture, the clay is preferably contacted with water prior to being contacted with the pesticide or the solvent in which the pesticide is dissolved. This preferred method is achieved by using a pre-formed aqueous dispersion of the clay or by adding the dry clay to the fertilizer solution before the emulsifiable concentrate is added. The uniformity of the dispersion can be improved by agitation using any conventional technique such as stirring, circulating, etc. The need for this agitation is dependent upon the quantity of clay used, the clay particle size, the length of time the dispersion remains in storage prior to use, etc. Agitation is also helpful in combining the aqueous clay dispersion with the emulsifiable pesticide concentrate, to form a more uniform emulsion and smaller droplets of the dispersed phase. These methods may be applied either at formulating plants or at actual field sites.

Although the attapulgite clay lessens the need for emulsifying agents, such agents are useful to provide further emulsion stability. Surface-active agents are the most common emulsifiers. Those in widest commercial use are the non-ionic and anionic agents, although cationic agents can also be used. Examples of non-ionic agents are long-chain alkyl and mercaptan polyethoxy alcohols, alkylaryl polyethoxy alcohols, sorbitan fatty esters, polyoxyethylene ethers, polyoxyethylene glycol esters, polyoxyethylene esters of fatty and resin acids, and mixtures of these. Examples of anionic agents are the calcium, amine, alkanolamine, and alkali salts of alkyl and alkylaryl sulfonates. Those most commonly used with fluid fertilizers include the ethoxylated and propoxylated mono- and diethers of phosphoric acid. The cationic agents include fatty amine blends, amine derivatives, and fatty alkylol amide condensates. Blends of non-ionic and anionic surface-active agents are of particular interest since the high degree of hydration which they create at the interfacial film is of particular benefit in stabilizing the emulsion.

The solvents used in the emulsifiable concentrates include those which are water-immiscible and those which are partially water-miscible, as well as those which are normally water-miscible when an organophosphorus pesticide is added. The solvents most frequently used in organophosphorus pesticide formulations are petroleum solvents such as xylenes and xylene derivatives, heavy aromatic naphthas, and kerosene. Other solvents include chlorobenzene, methylene chloride, ethylene dichloride and chlorotoluene. Any such solvents useful in traditional emulsifiable concentrates can be used in the present invention.

The relative quantities of the components of the present invention are not critical to the attainment of the improved result, since the improvement is achieved over a broad range of clay, fertilizer, and pesticide concentrations. In general, the relative quantities will be determined by the type of pesticide used, the type of fertilizer used, the crop to be fertilized, and the insects to be controlled, as well as general economic considerations.

It will be most convenient to use a quantity of clay which constitutes from about 0.1% to about 10.0% by weight of the aqueous phase of the final emulsion, or of the fertilizer solution if the fertilizer and clay are premixed prior to addition of the pesticide concentrate. The preferred clay concentration is from about 0.3% to about 3.0% by weight. Under certain conditions, the clay may interact with the pesticide to produce flocculation which may settle and detract from the uniformity of the emulsion. This can generally be eliminated, however, by adding additional clay to the emulsion.

Similarly, it will be most convenient to use a quantity of organophosphorus compound which constitutes from about 0.01% to about 10.0% by weight of the total emulsion, preferably from about 0.05% to about 5.0%. The emulsifiable concentrate generally contains from about 10% to about 90% by weight of the active ingredient, and most frequently from about 40% to about 70%.

The following examples are offered to illustrate the improvements attained by use of the present invention, and are not intended to limit or define the invention in any manner.

EXAMPLE 1

The following test data shows the improved results obtained from the addition of an attapulgite clay to a pesticide/fertilizer emulsifiable concentrate mixture.

Six different attapulgite clays were tested to demonstrate the general applicability of clays of the attapulgite type. The pesticide used in each case was O-ethyl-S-phenyl-ethylphosphonodithioate (known commercially as fonofos) in an emulsifiable concentrate of the following composition: pesticide, 47% by weight; heavy aromatic naphtha solvent, 45% by weight; and (phosphate ester)/(anionic emulsifying agent) blend, 8% by weight. The fertilizer used in each case was 8-24-6 liquid fertilizer.

According to the test procedure, the clay and fertilizer were thoroughly mixed by a laboratory centrifugal pump. The mixture was then poured into a 100-ml graduated cylinder up to a level corresponding to 97.5 ml. The emulsifiable pesticide concentrate was then added to bring the liquid level up to the 100-ml mark. The cylinder was then stoppered, inverted ten times, and placed in a location where it would be undisturbed so that periodic visual observations could be made. A control sample identical to the others but eliminating the use of clay was also tested and observed according to the same procedure.

The visual observations in each case consisted of noting the formation of cream and oil layers and recording their volumes. The formation of either or both of these layers indicates poor emulsion stability. The term "cream" refers to a region containing a higher proportion of the dispersed phase than the rest of the system. The cream layer is still an emulsion, since a dispersion still exists inside but formation of the cream layer indicates partial separation of the components of the emulsified composition and introduces nonuniformity to the system. The term "oil" refers to actual recombination of droplets of the dispersed phase to form a layer of solvent as a separate phase with pesticide dissolved therein.

The following clays were used:

| | |
|---|---|
| Attagel ® 350 | an attapulgite clay with sieve analysis: 34% +100 mesh 24% −325 mesh |
| Attaflow ® | an attapulgite clay dispersed in water-solids content 27% by weight, with residue sieve analysis: 99.6% −325 mesh |
| Attaclay ® X-250 | an attapulgite clay with sieve analysis: 85% −325 mesh |
| Attagel ® 40 | an attapulgite clay with average particle size 0.14 microns |
| Attapulgite 18/35 | an attapulgite granule of +35, −18 mesh particle size |
| Min-u-gel ® 200 | an attapulgite clay with sieve analysis: 95% −325 mesh |

All of the above clays are commercially available attapulgite-type clays. Min-u-gel 200 was obtained from Floridin Company, Pittsburgh, Pa., and the remainder were obtained from Engelhard Minerals and Chemicals Corporation, Edison, N.J. Attapulgite 18/35 is a granule which readily breaks down into small particles when placed in contact with water.

The test results are listed in Table I, which clearly shows that each sample which incorporated an attapulgite clay demonstrated a total absence of the oil layer and a reduction or elimination of the cream layer.

TABLE I

EMULSION STABILITY TESTS

Pesticide: O-Ethyl-S-phenyl-ethylphosphonodithioate
Fertilizer: 8-24-6
Clay: various attapulgite types

| | Cream/Oil Layers (ml) | | |
|---|---|---|---|
| | 1 hour | 2 hours | 4 hours |
| Control data - no clay present: | t/1.0 | 1.0/1.0 | 1.0/1.0 |
| Test data - 1.0 weight % clay added to fertilizer: | | | |
| Clay | | | |
| Attagel 350 | 0/0 | 0/0 | 0/0 |
| Attaflow | t/0 | t/0 | t/0 |
| Attaclay X-250 | 0/0 | 0/0 | 0/0 |
| Min-u-gel 200 | 0/0 | 0/0 | 0/0 |
| Attagel 40 | 0/0 | 0/0 | 0/0 |
| Attapulgite 18/35 | 0/0 | 0/0 | 0/0 |

Symbol "t" denotes trace amount.

EXAMPLE 2

This example shows that the improvement of the present invention is observable over a broad range of clay concentration. The procedures followed were identical to those of Example 1. The materials and quantities were similar to those of Example 1, except that two different formulations of the same pesticide were used:

Formulation A: emulsifiable concentrate—O-ethyl-S-phenyl-ethylphosphonodithioate, 49% by weight; xylenic solvent (petroleumderived fraction containing about 35% xylenes and about 65% aromatics and heavier components), 41% by weight; phosphate ester emulsifying agent, 10% by weight.

Formulation B: emulsifiable concentrate—O-ethyl-S-phenyl-ethylphosphonodithioate, 47% by weight; heavy aromatic naphtha, 45% by weight; (phosphate ester)/(anionic emulsifying agent) blend, 8% by weight.

Using Attaflow and two types of fertilizers, 10-34-0 and 8-24-6, the results obtained are shown in Table II, which indicates that cream and oil layers were eliminated at all clay concentrations tested.

TABLE II

EMULSION STABILITY TESTS

Pesticide: O-Ethyl-S-phenyl-ethylphosphonodithioate
Fertilizer: 10-34-0, 8-24-6
Clay: Attaflow at various concentrations

| Pesticide Formulation | Fertilizer | Clay Content | Cream/Oil Layers (ml) | | |
|---|---|---|---|---|---|
| | | | 1 hour | 2 hours | 4 hours |
| (Control Data) | | | | | |
| A | 10-34-0 | — | 1.5/1.5 | 1.0/2.0 | 2.0/2.0 |
| A | 8-24-6 | — | 0.5/1.5 | 0.5/2.0 | 0.5/2.0 |
| B | 10-34-0 | — | t/2.0 | t/2.0 | 0.5/2.0 |
| B | 8-24-6 | — | t/1.0 | 1.0/1.0 | 1.0/1.0 |
| (Test Data) | | | | | |
| A | 10-34-0 | 0.3 | 0/t | 0/t | 0/0 |
| A | 10-34-0 | 0.6 | 0/0 | 0/0 | 0/0 |
| A | 10-34-0 | 1.0 | 0/0 | 0/0 | 0/0 |
| A | 10-34-0 | 1.2 | 0/0 | 0/0 | 0/0* |
| A | 10-34-0 | 1.4 | 0/0 | 0/0 | 0/0* |
| A | 10-34-0 | 1.6 | 0/0 | 0/0 | 0/0 |

TABLE II-continued
EMULSION STABILITY TESTS

Pesticide: O-Ethyl-S-phenyl-ethylphosphonodithioate
Fertilizer: 10-34-0, 8-24-6
Clay: Attaflow at various concentrations

| Pesticide Formulation | Fertilizer | Clay Content | Cream/Oil Layers (ml) 1 hour | 2 hours | 4 hours |
|---|---|---|---|---|---|
| A | 10-34-0 | 2.0 | 0/0 | 0/0 | 0/0 |
| A | 10-34-0 | 3.0 | 0/0 | 0/0 | 0/0 |
| A | 8-24-6 | 0.4 | 0/0* | 0/0* | 0/0* |
| A | 8-24-6 | 0.6 | 0/0* | 0/0* | 0/0* |
| A | 8-24-6 | 0.8 | 0/0 | 0/0 | 0/0 |
| A | 8-24-6 | 1.0 | 0/0 | 0/0 | 0/0 |
| A | 8-24-6 | 1.2 | 0/0 | 0/0 | 0/0 |
| A | 8-24-6 | 1.5 | 0/0 | 0/0 | 0/0 |
| B | 10-34-0 | 0.8 | 0/0 | 0/0* | 0/0* |
| B | 10-34-0 | 1.0 | 0/0 | 0/0 | 0/0 |
| B | 10-34-0 | 1.2 | 0/0 | 0/0 | 0/0 |
| B | 10-34-0 | 1.4 | 0/0 | 0/0 | 0/0 |
| B | 10-34-0 | 1.6 | 0/0 | 0/0 | 0/0 |
| B | 10-34-0 | 2.0 | 0/0 | 0/0 | 0/0 |
| B | 10-34-0 | 3.0 | 0/0 | 0/0 | 0/0 |
| B | 8-24-6 | 0.4 | 0/0 | 0/0 | 0/0 |
| B | 8-24-6 | 0.6 | 0/0 | 0/0 | 0/0 |
| B | 8-24-6 | 0.8 | 0/0 | 0/0 | 0/0 |
| B | 8-24-6 | 1.0 | 0/0 | 0/0 | 0/0 |
| B | 8-24-6 | 1.2 | 0/0 | 0/0 | 0/0 |

NOTES:
Clay content is expressed as weight percent of total mixture.
Symbol "t" denotes trace amount.
Symbol "*" denotes occurrence of flocculation.

EXAMPLE 3

This example demonstrates the efficacy of the present invention over a broad range of fertilizers. Again, the procedures of Example 1 were followed, although six different liquid fertilizers were used. Pesticide Formulation A of Example 2, and the predispersed attapulgite-type clay Attaflow were used in all tests. The results are shown in Table III, which indicates complete elimination of cream and oil layers in every case.

TABLE III
EMULSION STABILITY TESTS

Pesticide: O-Ethyl-S-phenyl-ethylphosphonodithioate
Fertilizer: various
Clay: Attaflow, approximately 1.0 weight % of total

| Fertilizer | Control (no clay) 1 hour | 4 hours | Test (clay present) 1 hour | 4 hours |
|---|---|---|---|---|
| 16-16-4 | 2.0/0 | 2.0/0 | 0/0 | 0/0* |
| 7-21-7 | 1.0/2.0 | 1.0/2.5 | 0/0 | 0/0* |
| 4-10-10 | 0/t | 6.0/2.0 | 0/0* | 0/0* |
| 19-19-0 | 3.0/0 | 3.0/0 | 0/0 | 0/0 |
| 20-10-0 | 1.5/0 | * | t/0 | t/0 |
| 9-27-5 | 3.0/1.5 | 3.0/1.5 | 0/0 | 0/0 |

NOTES:
Symbol "t" denotes tract amount
Symbol "*" denotes occurrence of flocculation

EXAMPLE 4

This example demonstrates the efficacy of the present invention over a broad range of insecticide concentration. Again, the procedures of Example 1 were followed, this time varying the quantity of pesticide formulation rather than using a fixed quantity of 2.5 ml. Both Formulations A and B of Example 2 were used, together with 10-34-0 and 8-24-6 fertilizers, and the predispersed attapulgite clay Attaflow at approximately 1% by weight of the total mixture. The results, shown in Table IV, indicate the complete elimination of cream and oil layers at every concentration.

TABLE IV
EMULSION STABILITY TESTS

Pesticide: O-Ethyl-O-phenyl-ethylphosphonodithioate at various concentrations
Fertilizer: 10-34-0, 8-24-6
Clay: Attaflow, approximately 1.0 weight

| Pesticide Formulation | % of total Pesticide Amount | Fertilizer | Cream/Oil Layers (ml) 1 hour | 4 hours |
|---|---|---|---|---|
| (Control Data) | | | | |
| A | 2.5 | 10-34-0 | 1.5/1.5 | 2.0/2.0 |
| A | 2.5 | 8-24-6 | 0.5/1.5 | 0.5/2.0 |
| B | 2.5 | 10-34-0 | t/2.0 | 0.5/2.0 |
| B | 2.5 | 8-24-6 | t/1.0 | 1.0/1.0 |
| (Test Data) | | | | |
| A | 1.0 | 10-34-0 | 0/0 | 0/0 |
| A | 2.0 | 10-34-0 | 0/0 | 0/0 |
| A | 3.0 | 10-34-0 | 0/0 | 0/0 |
| A | 4.0 | 10-34-0 | 0/0 | 0/0 |
| A | 1.0 | 8-24-6 | 0/0 | 0/0 |
| A | 2.0 | 8-24-6 | 0/0 | 0/0* |
| A | 3.0 | 8-24-6 | 0/0 | 0/0* |
| A | 4.0 | 8-24-6 | 0/0 | 0/0* |
| B | 1.0 | 10-34-0 | 0/0 | 0/0 |
| B | 2.0 | 10-34-0 | 0/0 | 0/0 |
| B | 4.0 | 10-34-0 | 0/0 | 0/0* |
| B | 4.0 | 10-34-0 | 0/0 | 0/0* |
| B | 1.0 | 8-24-6 | 0/0 | 0/0 |
| B | 2.0 | 8-24-6 | 0/0 | 0/0 |
| B | 3.0 | 8-24-6 | 0/0 | 0/0 |
| B | 4.0 | 8-24-6 | 0/0 | 0/0 |

NOTES:
Pesticide amount is expressed as volume percent of concentrate with respect to total mixture (equivalent to ml)
Symbol "*" denotes occurrence of flocculation
Symbol "t" denotes trace amount

EXAMPLE 5

This example demonstrates the efficacy of the present invention over a broad range of organophosphorus insecticides. The procedures of Example 1 were followed, using five commercially available pesticides:

O,O-Diethyl-S[2-(ethylthio)-ethyl]phosphorodithioate, common name disulfoton, trade name DI-SYSTON-®—obtained from Mobay Chemical Corporation, Kansas City, Mo.—as emulsifiable concentrate containing 6 lb active ingredient per gallon (0.72 kg/l)

O,O-Diethyl-O-(p-methylsulfinylphenyl) phosphorothioate, common name fensulfothion, trade name DASANIT®—obtained from Mobay Chemical Corporation—as emulsifiable concentrate containing 6 lb active ingredient per gallon (0.72 kg/l)

O-Ethyl-S,S-dipropylphosphorodithioate, common name ethoprop, trade name MOCAP®—obtained from Mobil Chemical Company, Richmond, Va.—as emulsifiable concentrate containing 6 lb active ingredient per gallon (0.72 kg/l)

O,O-Dimethyl O-p-nitrophenyl phosphorothioate, common name methyl parathion—obtained from Stauffer Chemical Company—as 4 lb/gal (0.48 kg/l) emulsifiable concentrate S-[(p-Chlorophenyl)thio]methyl O,O-diethyl phosphorodithioate, common name carbophenothion, trade name TRITHION—obtained from Stauffer Chemical Company—as 4 lb/gal (0.48 kg/l) and 8 lb/gal (0.96 kg/l) emulsifiable concentrate.

Fertilizers 10-34-0 and 8-24-6 were used with the predispersed attapulgite clay Attaflow at approximately 1% by weight of the total mixture. The results, shown in Table V, indicate almost complete elimination of cream and oil layers in each case.

TABLE V

EMULSION STABILITY TESTS

Pesticide: various organophosphorus compounds
Fertilizers: 10-34-0, 8-24-6
Clay: Attaflow, approximately 1.0 weight % of total except where indicated

| Pesticide | Fertilizer | Cream/Oil Layers (ml) | | | |
|---|---|---|---|---|---|
| | | Control (no clay) | | Test (clay present) | |
| | | 1 hour | 4 hours | 1 hour | 4 hours |
| MOCAP | 10-34-0 | 0.5/1.5 | 0.5/1.5 | 0/t | 0/t |
| | 8-24-6 | 0.5/1.5 | 0.5/2.0 | 0/0 | 0/0 |
| DI-SYSTON | 10-34-0 | 0.5/1.5 | 0.5/1.5 | 0/t | 0/t |
| | 8-24-6 | t/2.0 | t/2.0 | 0/0 | 0/t |
| DASANIT | 10-34-0 | 0.5/1.5 | 0.5/1.5 | 0/t | 0/t |
| | 8-24-6 | 1.0/1.5 | 1.0/1.5 | 0/0 | 0/0 |
| PARATHION | 10-34-0 | 0/3.0 | 0/3.0 | 0/1.0* | 0/1.25* |
| | 8-24-6 | 0/2.0 | 0/2.5 | 0/t | 0/t |
| TRITHION 4 lb/gal | 10-34-0 | 0/4.0 | 0/4.0 | 0/1.5* | 0/1.75* |
| | 8-24-6 | 0/2.5 | 0/2.75 | 0/t* | 0/t* |
| TRITHION 8 lb/gal | 10-34-0 | 0/3.0 | 0/3.5 | 0/t | 0/0.25 |
| | 8-24-6 | 0/2.0 | 0/2.5 | t/0 | t/0 |

NOTES:
Symbol "t" denotes trace amount.
Asterisk denotes clay concentration of 2% rather than 1%

METHODS OF APPLICATION

In general, any conventional method of application of a liquid composition can be used in applying the compositions of the present invention to a field. The locus of application can be soil, seeds, seedlings, or the actual crop plants, as well as flooded fields. Typical application methods include the use of boom sprayers, hand-held sprayers, and airplane-mounted sprayers, as well as direct furrow application from a planting tractor, as in the "split-boot" technique described above.

The compositions can also be applied to the soil through irrigation systems. According to this technique, the compositions are added directly to irrigation water immediately prior to irrigation of the field. This technique is applicable in all geographical areas regardless of rainfall, since it permits supplementation of the natural rainfall at critical stages of plant growth. The irrigation water can be applied by the use of sprinkler systems, surface furrows, or flooding. Such application is most effectively done before the weeds germinate, either early in the spring prior to germination or within two days after cultivation of the field.

The amount of composition which constitutes an insecticidally effective and crop growth enhancing amount depends upon the nature of the insects to be controlled and the crop to be grown. The rate of application of each ingredient varies from about 0.01 to about 500 pounds per acre, preferably about 0.1 to about 50 pounds per acre with the actual amount used depending on the overall cost and the desired results. It will be readily apparent to one skilled in the art that compositions exhibiting lower insecticidal activity will require a higher dosage rate for the same degree of control than more active compositions.

What is claimed is:

1. An emulsion composition comprising:
   (a) an aqueous solution of an N-P or N-P-K fertilizer,
   (b) an attapulgite clay, and
   (c) an organic solution comprising a water-immiscible or partially water-miscible solvent and a pesticidal organophosphorus compound of the formula

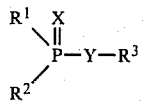

in which
   $R^1$ is selected from the group consisting of $C_1$-$C_6$ alkyl, $C_1$-$C_6$ alkoxy, and $C_1$-$C_6$ alkylthio,
   $R^2$ is selected from the group consisting of $C_1$-$C_6$ alkyl, $C_1$-$C_6$ alkoxy, and $C_1$-$C_6$ alkylthio,
   $R^3$ is selected from the group consisting of $C_1$-$C_6$ alkyl, $C_2$-$C_8$ alkylthioalkyl, phenyl, and $C_7$-$C_{12}$ phenylthioalkyl, the phenyl rings optionally substituted with halogen, $C_1$-$C_3$ alkyl, nitro or $C_1$-$C_3$ alkylsulfinyl,
   X is oxygen or sulfur, and
   Y is oxygen or sulfur.

2. A composition according to claim 1 in which the organophosphorus compound is defined such that:
   $R^1$ is selected from the group consisting of $C_1$-$C_4$ alkoxy and $C_1$-$C_4$ alkylthio,
   $R^2$ is selected from the group consisting of $C_1$-$C_4$ alkyl, $C_1$-$C_4$ alkoxy, and $C_1$-$C_4$ alkylthio,
   $R^3$ is selected from the group consisting of $C_1$-$C_3$ alkyl, $C_2$-$C_6$ alkylthioalkyl, phenyl, and $C_7$-$C_9$ phenylthioalkyl, the phenyl rings optionally substituted with halogen, $C_1$-$C_3$ alkyl, nitro, or $C_1$-$C_3$ alkylsulfinyl,
   X is oxygen or sulfur, and
   Y is oxygen or sulfur.

3. A composition according to claim 1 in which the organophosphorus compound is O-ethyl-S-phenylethylphosphonodithioate.

4. A composition according to claim 1 in which the organophosphorus compound is O,O-diethyl-S[(2-ethylthio)-ethyl]phosphorodithioate.

5. A composition according to claim 1 in which the organophosphorus compound is O,O-diethyl-O-(p-methylsulfinylphenyl) phosphorothioate.

6. A composition according to claim 1 in which the organophosphorus compound is O-ethyl-S,S-dipropylphosphorodithioate.

7. A composition according to claim 1 in which the organophosphorus compound is O,O-dimethyl-O-p-nitrophenyl phosphorothioate.

8. A composition according to claim 1 in which the organophosphorus compound is S-[(p-chlorophenyl)thio]methyl O,O-diethylphosphorodithioate.

9. A composition according to claims 1, 2, 3, 4, 5, 6, 7, or 8 in which the organophosphorus compound constitutes from about 0.01% to about 10% by weight of the composition.

10. A composition according to claims 1, 2, 3, 4, 5, 6, 7, or 8 in which the organophosphorus compound constitutes from about 0.05% to about 5% by weight of the composition.

11. A composition according to claims 1, 2, 3, 4, 5, 6, 7, or 8 in which the water-immiscible or partially water-miscible solvent is selected from petroleum solvents, heavy aromatic naphthas, and kerosene.

12. A composition according to claims 1, 2, 3, 4, 5, 6, 7, or 8 further comprising a surface active agent.

13. A composition according to claims 1, 2, 3, 4, 5, 6, 7, or 8 in which the water-immiscible or partially water-miscible solvent is selected from petroleum solvents, heavy aromatic naphthas, and kerosene; and which further comprises a surface active agent which is a nonionic or anionic type or a blend of nonionic and anionic types.

* * * * *